United States Patent [19]

Thalheimer

[11] Patent Number: 4,721,466

[45] Date of Patent: Jan. 26, 1988

[54] TOOTH BLOCKS

[76] Inventor: Roland Thalheimer, 9437 Oakwood Manor La., St. Louis, Mo. 63126

[21] Appl. No.: 851,941

[22] Filed: Apr. 14, 1986

[51] Int. Cl.⁴ .............................................. A61C 13/00
[52] U.S. Cl. .................................. 433/171; 433/199.1; 433/213; 433/26; 433/74
[58] Field of Search ................ 433/199.1, 26, 74, 213, 433/171.0

[56] References Cited

U.S. PATENT DOCUMENTS 1,071,952  9/1913  Perzin .............................. 433/199.1
1,483,781  2/1924  Churchill ......................... 433/199.1
3,335,495  8/1967  Wichner .............................. 433/171

*Primary Examiner*—Richard J. Scanlan, Jr.
*Attorney, Agent, or Firm*—Joseph A. Fenlon

[57] ABSTRACT

A tooth-block for fabrication of dentures, including a horizontally deformable bar of rectangular cross-section provided along its upper margin with outwardly projecting retentions, each retention having an individual artificial tooth securely mounted thereon in spaced separation from the bar, each retention and its respective tooth being selectively positional with respect to the bar and to each other tooth.

1 Claim, 3 Drawing Figures

TOOTH BLOCKS

It is the object of this invention to provide a means and method for constructing arrays of artificial pre-sized and pre-set tooth-blocks which are deformable to conform with the Curve of Spee, which are stronger and more resistant to breakage, which are provided with teeth that are selectively positionable with respect to each other, and which eliminate the need for lengthy, time consuming manual assembly procedures.

With the above and other objects in mind, which iwll become immediately more apparent upon reading and examining this application, my invention resides in the unique and novel form, arrangement, combination and construction of the various elements and steps described in the specification, shown in the drawingins and claimed in the claims.

IN THE DRAWINGS

Figure 1:
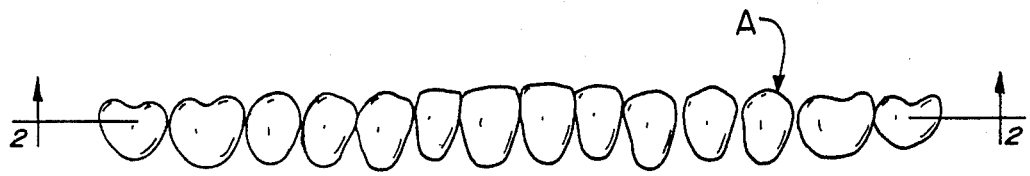
FIG. 1 is a front elevational view of a preferred embodiment of my toothblock.
Figure 2:
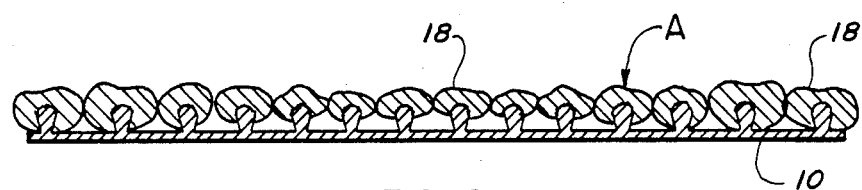
FIG. 2 is a sectional view taken along lines 2—2 of FIG. 1.
Figure 3:
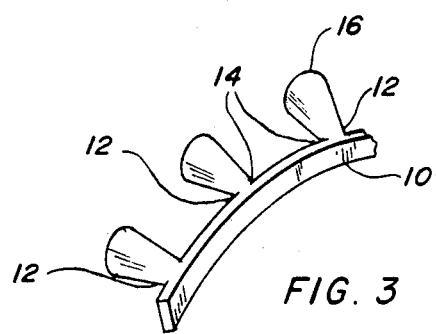
FIG. 3 is a special view showing an enlarged fragmentary section of the lingual bar and retentions.

Referring now in more detail and by reference character to the drawings which illustrate a preferred embodiment of the invention, A designates a tooth-block comprising an elongated lingual bar 10 fabricated of deformable material and having rectangular cross section which is substantially larger in height than in thickness. Integrally provided along the bar 10 and projecting horizontally outwardly therefrom along the upper margin thereof is a plurality of spaced retentions 12, each retention being diametrally smaller at the common margin 14 with the bar 10. Each retention 12 is provided with an enlarged outer end 16. Securely molded to the outer end 16 of each retention 12 is an artificial tooth 18, each retention 12 being sized to provide a slight separation between each tooth 18 and the lingual bar 10 to permit selective positioning of each tooth 18 with respect to the bar 10 and each other tooth 18.

USE

In use, the tooth-block A is provided to the dentist with the bar 10 in curved form with each of the teeth 18 securely attached to a separate retention 12. Although each tooth 18 is shown to be similar to each other tooth 18, the individual teeth 18 shown on the block A are preferably varied in shape and size to conform to the appearance of natural teeth. The teeth 18 are separated from the bar 10 and each other so that each tooth 18 may be selectively positioned with respect to the bar and each other tooth, the shape of the retention serving to hold its molded tooth firmly thereon during adjustment. The dentist, by selectively deforming preselected retentions can create or match any natural tooth appearance simply, such as gaps and slight overlapping to take away the artificial appearance.

When the dentist has selected the appropriate size of the block A for the patient, the dentist makes a wax mold (not shown) and deforms the bar 10 to conform to the contour of the patient's mouth. Thereafter, by selectively pivoting and twisting the tooth 18 and its retention 12 as a unit with respect to the bar 10, the dentist may selectively adjust the position of any tooth 18 with respect to the deformed bar 10, can selectively vary the space of the individual teeth with respect to each other, may selectively provide spaced gaps in the individual's teeth, and references the block in the mold. When the molds and tooth block are sent to the technician, the technician, in our simple, time saving operation, can set the block A in the mold and prepare the finished denture for the dentist in one simple operation, thereby eliminating the previous time consuming effort (usually several hours) required to place the teeth individually by hand. Many lab hours are thus saved and the cost of the denture to the patient is substantially reduced.

It should be readily apparent that the tooth-block A as above described represents a substantial improvement in laboratory assembly and adjustment time and permits a substantial cost reducer to the consumer.

It should be further apparent that the techniques and structures described above are equally adaptable to the manufacture and assembly of partial dentures.

Having thus described by invention, I claim:

1. A tooth block comprising a horizontal bar which is horizontally deformable and includes a plurality of outwardly extending deformable retentions, each of said retentions being smaller in cross section at the bar than outwardly therefrom, and a plurality of artificial teeth, each tooth being fixedly mounted on an individual retention in spaced separation from the bar and from each other tooth and being movable therewith as its retention is selectively positioned with respect to the horizontal axis of the bar, whereby each tooth and its respective retention may be selectively positioned and held securely with respect to the bar and each other tooth independent of the movement and positioning of every other tooth and its respective retention.

* * * * *